(12) United States Patent
Korathu-Larson

(10) Patent No.: US 12,350,889 B2
(45) Date of Patent: Jul. 8, 2025

(54) 3D AXIAL GROWTH OBJECT, AND APPARATUS FOR AND METHOD OF MAKING THEREOF

(71) Applicant: Rory Korathu-Larson, LLC, Seattle, WA (US)

(72) Inventor: Rory Korathu-Larson, Seattle, WA (US)

(73) Assignee: Rory Korathu-Larson, LLC, Seattle, WA (US)

( * ) Notice: Subject to any disclaimer, the term of this patent is extended or adjusted under 35 U.S.C. 154(b) by 611 days.

(21) Appl. No.: 17/561,057

(22) Filed: Dec. 23, 2021

(65) Prior Publication Data

US 2022/0194013 A1  Jun. 23, 2022

Related U.S. Application Data

(60) Provisional application No. 63/130,395, filed on Dec. 23, 2020.

(51) Int. Cl.
| | |
|---|---|
| *B29C 64/40* | (2017.01) |
| *B29C 64/124* | (2017.01) |
| *B29C 64/364* | (2017.01) |
| *B33Y 10/00* | (2015.01) |
| *B33Y 30/00* | (2015.01) |
| *B33Y 40/00* | (2020.01) |
| *B33Y 80/00* | (2015.01) |

(52) U.S. Cl.
CPC ............ *B29C 64/40* (2017.08); *B29C 64/124* (2017.08); *B29C 64/364* (2017.08); *B33Y 10/00* (2014.12); *B33Y 30/00* (2014.12); *B33Y 40/00* (2014.12); *B33Y 80/00* (2014.12); *B29K 2995/0056* (2013.01)

(58) Field of Classification Search
CPC ..... B29C 64/40; B29C 64/124; B29C 64/364; B33Y 10/00; B33Y 30/00; B33Y 40/00; B33Y 80/00; B29K 2995/0056; C12M 25/14; C12M 33/00; B05D 1/18; A61F 2/91; A61F 2210/0076
See application file for complete search history.

(56) References Cited

U.S. PATENT DOCUMENTS

2020/0197976 A1\*  6/2020  Dufort .................... B29C 71/04

OTHER PUBLICATIONS

Wang et al. ("Freestanding hierarchical vascular structures engineered from ice", Biomaterials 192 (2019) 334-345) (Year: 2019).\*

\* cited by examiner

*Primary Examiner* — Galen H Hauth
*Assistant Examiner* — Baileigh Kate Darnell
(74) *Attorney, Agent, or Firm* — Timothy J. Billick; Robert Roth

(57) ABSTRACT

A 3D object including a support structure formed with a mesh layer and an intermediate support structure; and one or more additive layers of substrate material formed via an axial growth process in which the substrate material formed a film over mesh holes in the mesh layer, thereby forming a continuous surface where the mesh holed previously existed.

6 Claims, 9 Drawing Sheets

3D AXIAL GROWTH OBJECT, AND APPARATUS FOR AND METHOD OF MAKING THEREOF

CROSS REFERENCE TO RELATED PATENT APPLICATIONS

The application claims priority to U.S. Provisional Patent Application No. 63/130,395 filed Dec. 23, 2020, entitled "3D AXIAL GROWTH PRINTING APPARATUS AND METHOD THEREOF," and incorporates the contents thereof in its entirety by reference.

BACKGROUND

The idea of 3D printing has been around at least since the 1950s. However, it is generally accepted that the first viable 3D printer was not actually created until the 1970s. Since then, the field of 3D printing has gained steam and improved vastly. Technological capabilities of the field have advances even as early as 2012 to include the ability to assist in the fabrication of biological components. Nevertheless, the advances in the field of 3D printing have yet to fully replicate large, viable organs, for example, and some organic components remain challenging to replicate regardless of size, for myriad reasons.

In addition to the opportunity for improving 3D printing and 3D print-inclusive additive manufacturing for biological purposes, there further remain similar challenges in metal, plastic, and other material-based 3D printing technologies with respect to strength and resilience of the structures created.

Many of the existing processes and machines for creating 3D printed objects rely on an apical growth method of creation, which method is generally described by a build rate with respect to the surface area.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Furthermore, the drawings may be considered as providing an approximate depiction of the relative sizes of the individual components within individual figures. However, the drawings are not to scale, and the relative sizes of the individual components, both within individual figures and between the different figures, may vary from what is depicted. In particular, some of the figures may depict components as a certain size or shape, while other figures may depict the same components on a larger scale or differently shaped for the sake of clarity.

DETAILED DESCRIPTION

Overview

Figure 1:
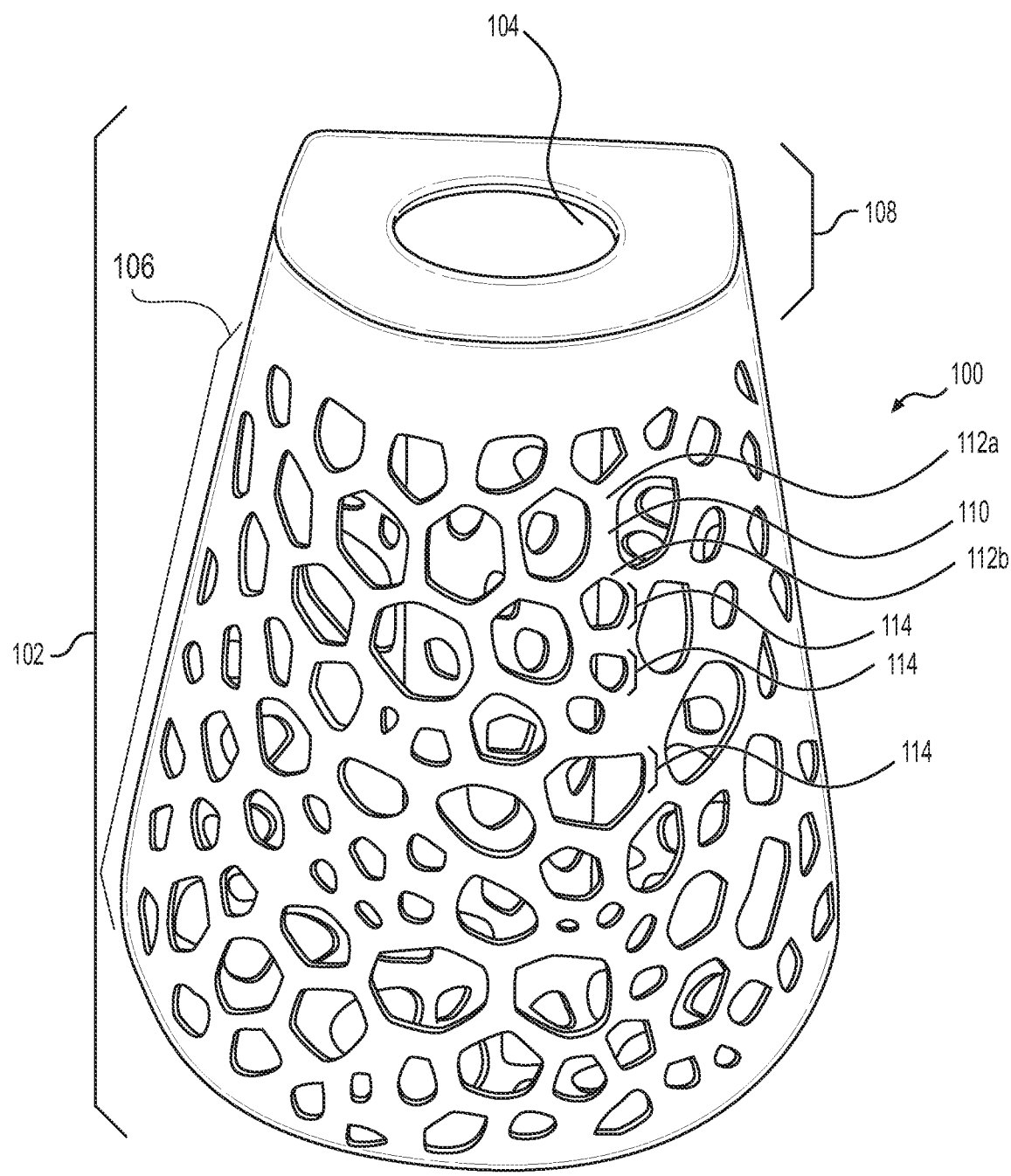
FIG. 1 illustrates a perspective view of an example embodiment of a support structure according to an embodiment of the instant disclosure.

This disclosure is directed in part to a system (e.g., machine, apparatus, componentry, etc.) including one or more features for forming 3-dimensional objects (e.g., structures, components, biological and/or non-biological parts, apparatuses, etc.). The 3-dimensional objects include an underlying support structure and one or more additive material layers disposed on the support structure. Additionally, this disclosure is directed in part to a method (e.g., process, steps, etc.) for forming the aforementioned 3-dimensional objects including an underlying support structure and one or more additive material layers on the support structure, which method may include the algorithmic methodology implemented with the system to create the entirety of such objects and/or divisible portions thereof, or to provide the phases through which one or more components thereof may endure to create such objects mentioned above. Additionally, this disclosure is directed in part to the creation of an underlying 3-dimensional support structure configured to accept one or more additive material layers on the support structure. Moreover, this disclosure is also directed in part to the 3-dimensional objects that are made by the aforementioned system and/or method, or which may be made by any other system and/or method that results in the creation of a 3-dimensional object like that described hereinafter.

In an embodiment, a 3-dimensional object formed as disclosed may exhibit one or more of increased strength, resilience, durability, or flexibility properties, among other properties.

This disclosure is further be directed in part to the elemental components of the underlying structure and/or the one or more additive material layers used to create the 3-dimensional objects.

Illustrative Embodiments

An axial growth process to create a 3-dimensional object ("3D object"), a system with which to implement the process, and the 3D object created thereby, are all disclosed herein.

Note, while a conventional 3D-printer is considered to be particularly well-suited for the creation of a support structure as disclosed (see below) and is thus a primary example discussed as a part of the manufacturing process herein, the use of the term "3D" in conjunction with the aforementioned "3D object" is not an implication that every 3D object, or sub-component thereof, is or might only be formed via a 3D-printer. Rather, the expression of "3D" is intended to merely connote that the objects discussed specifically have a three-dimensional shape and profile. Nevertheless, in an embodiment, using the innovative techniques and developments described hereinafter, a conventional 3D-printer may be used, with or without modification, in order to create, or assist in the creation of, one or more parts/features/portions/components/aspects of the 3D object defined according to the disclosed techniques and desired traits.

Thus, a 3D object formed via the axial growth process may be defined, at least in part, by the process and/or machinery used to create the 3D object, as it is believed that the process may impart important characteristics to the 3D object. Moreover, a 3D object formed via the axial growth process may further be defined, at least in part, by the materials being added to the support structure, (which may be added, for example, by a volume rate).

Figure 2:
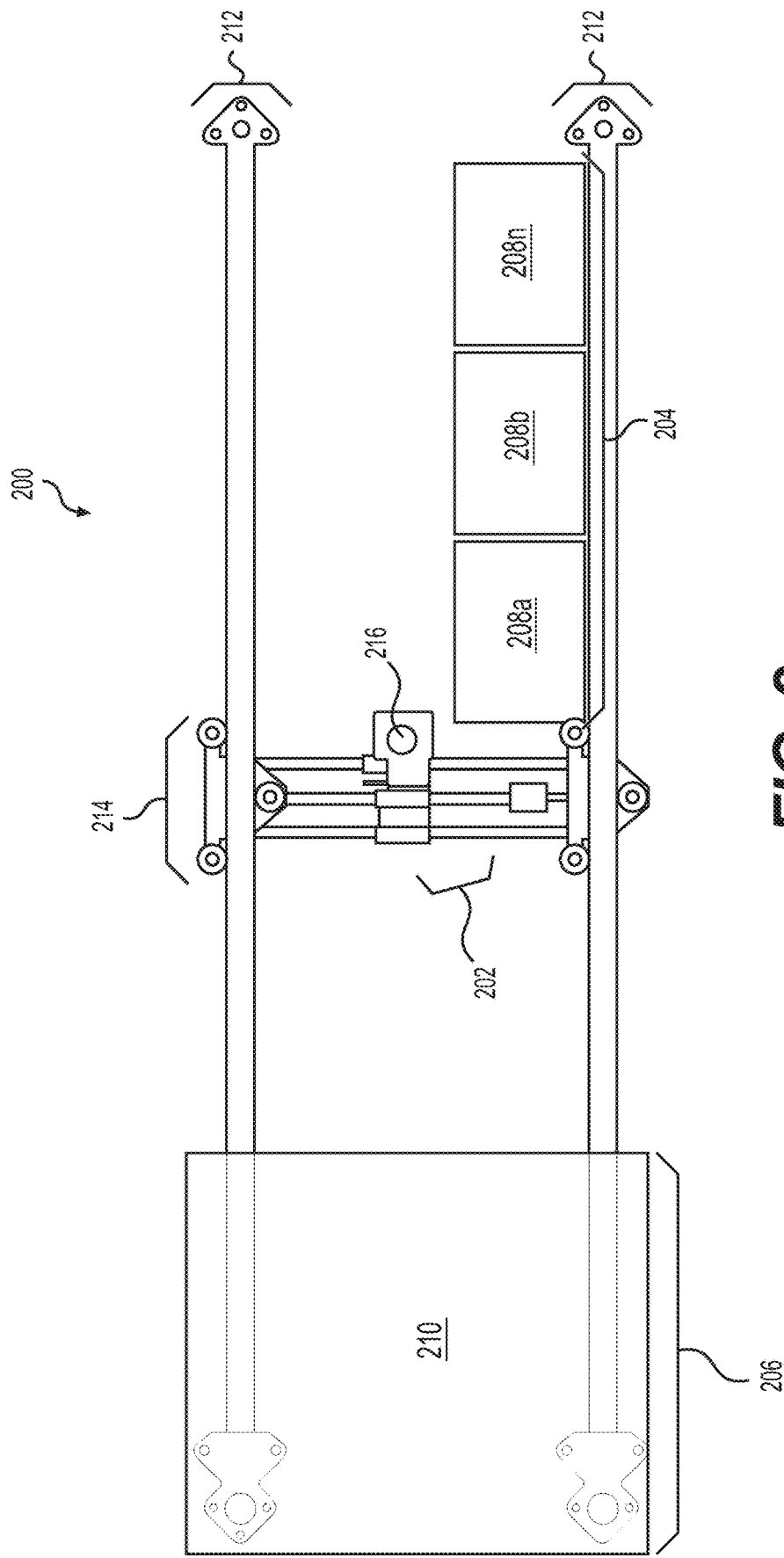
FIG. 2 illustrates a schematic embodiment of a system for processing support structures to form 3D objects, according to an embodiment of the instant disclosure.
Figure 3A:
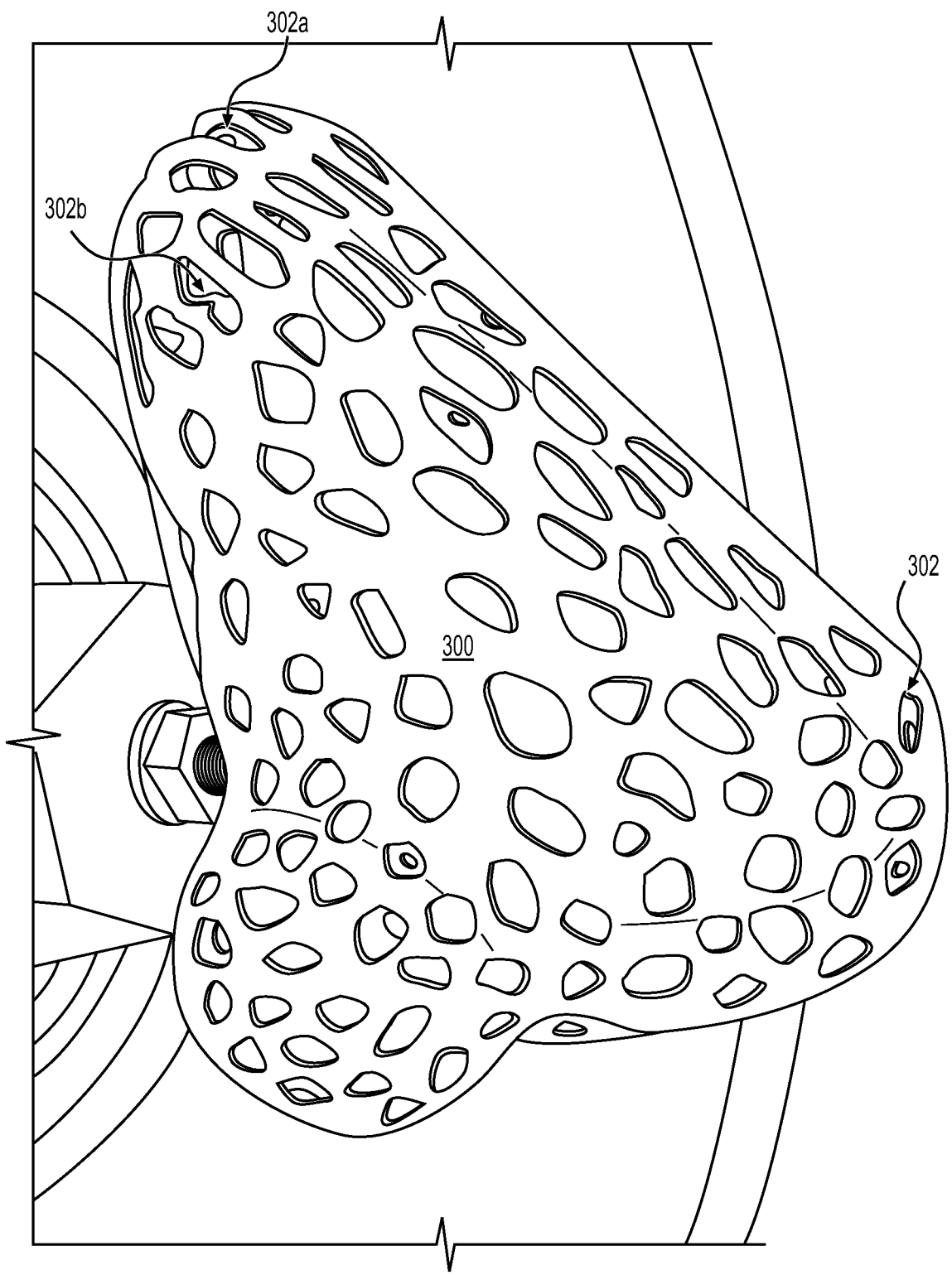
FIG. 3A illustrates a perspective view of an embodiment of another support structure, used to form a representation of a replacement human nose, prior to additional processing via the system of FIG. 2, according to an embodiment of the instant disclosure.
Figure 3B:
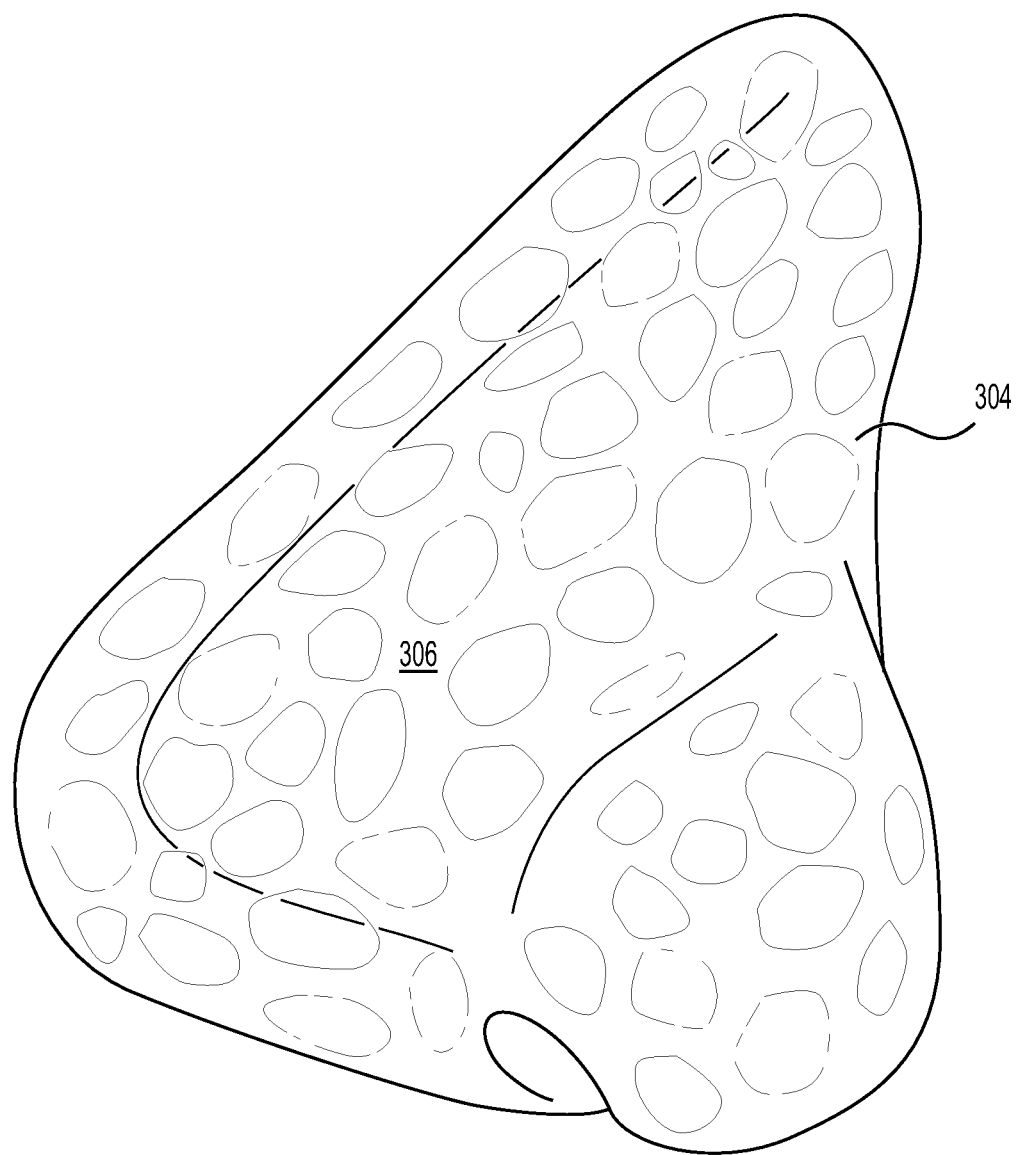
FIG. 3B illustrates a perspective view of an embodiment of the human nose (3D object) after the support structure of FIG. 3A has been processed via the system of FIG. 2, according to an embodiment of the instant disclosure.

In an embodiment, a 3D object may include an underlying support structure (e.g., scaffold, template, frame, skeleton, shell, base, etc.), such as an example support structure 100, as depicted in FIG. 1, and one or more additive material layers on the support structure (see FIG. 3B, for example). Such a 3D object may be formed using a system 200 (e.g., machine, device, collaboration of mechanical/electrical hardware and/or software components), as seen in FIG. 2. The system 200 may include one or more of the following components either collaboratively (as depicted) or independently, as each component is easily separable and independently operable, as one skilled in the art would understand. That is, in an embodiment, the system 200 may include one or more of: a manufacturing unit 202, a substrate application unit 204, or a developing unit 206. Nevertheless, there may be advantages to an embodiment of a system that includes all of the aforementioned features.

In an embodiment, the manufacturing unit 202 may include one or more of: a 3D printer device (conventional or specially modified), a molding device, or other capable manufacturing device. The manufacturing unit 202 may manufacture the support structure 100 in whole or in part, or may merely be configured to secure a prefabricated version of the support structure 100 so as to assist in the manufacture of the 3D object.

The substrate application unit 204 may include one or more containers 208a, 208b, 208n, sized to accept the support structure 100 therein. The one or more containers 208a, 208b, 208n may have disposed therein, or may be configured to have released therein, a substrate, such as substrate A, substrate B, and/or substrate C, as depicted, so as to allow contact application of a predetermined substrate onto the support structure 100, when the support structure 100 is placed therein. Notably, "A," "B," and "C," may denote that the substrate materials are distinguished only for the purpose of performing a series of successive applications to the support structure 100. Alternatively, "A," "B," and "C," may denote that the substrate materials are distinguished as distinct materials. Moreover, substrate materials A, B, and C may be, all or respectively, in one or more physical states, such as liquid, gelatin, powder, aerosol, etc. Thus, the substrate material(s) are provided such that the support structure 100 may be: dipped into the substrate, or otherwise positioned to have the substrate sprayed, poured, blown, or dusted thereon, according to the properties associated with the choice of the substrate. It is understood that the choice of substrate to be applied may depend at least in part on one or more of: user preference, intended use of the final 3D object, biocompatibility, compatibility with the material of the support structure 100, chemical interactivity between the support structure 100 and the substrate material, curing time, etc.

The developing unit 206 may include a chamber 210 (e.g., enclosed or unenclosed area, space, room, environment-controlled location) in which any curing, drying, finalizing, etc. of the support structure 100 or the 3D object, whether in an intermediate or final state, may occur. As indicated above, in an embodiment, the environment within the chamber 210 may be controlled to accommodate the corresponding process aspects (e.g., curing or drying times/temperatures of any substrate applied on the support structure, etc.) of the interaction or state of the substrate materials with respect to the support structure accordingly. Moreover, the developing unit 206 may include a plurality of chambers 210, or may subdivided into compartmental portions within the chamber 210 into which one or more support structures (such as one or more support structures 100) may be placed for varying stages of completion of the 3D object desired.

In an embodiment, the chamber 210 may include a UV light, a heating element, and/or well circulated air, etc. to aid in the hardening process (e.g., solidification of the film of additive material layers). Notably, spinning and tilting the object while it hardens may result in further closed cells.

Figure 5:
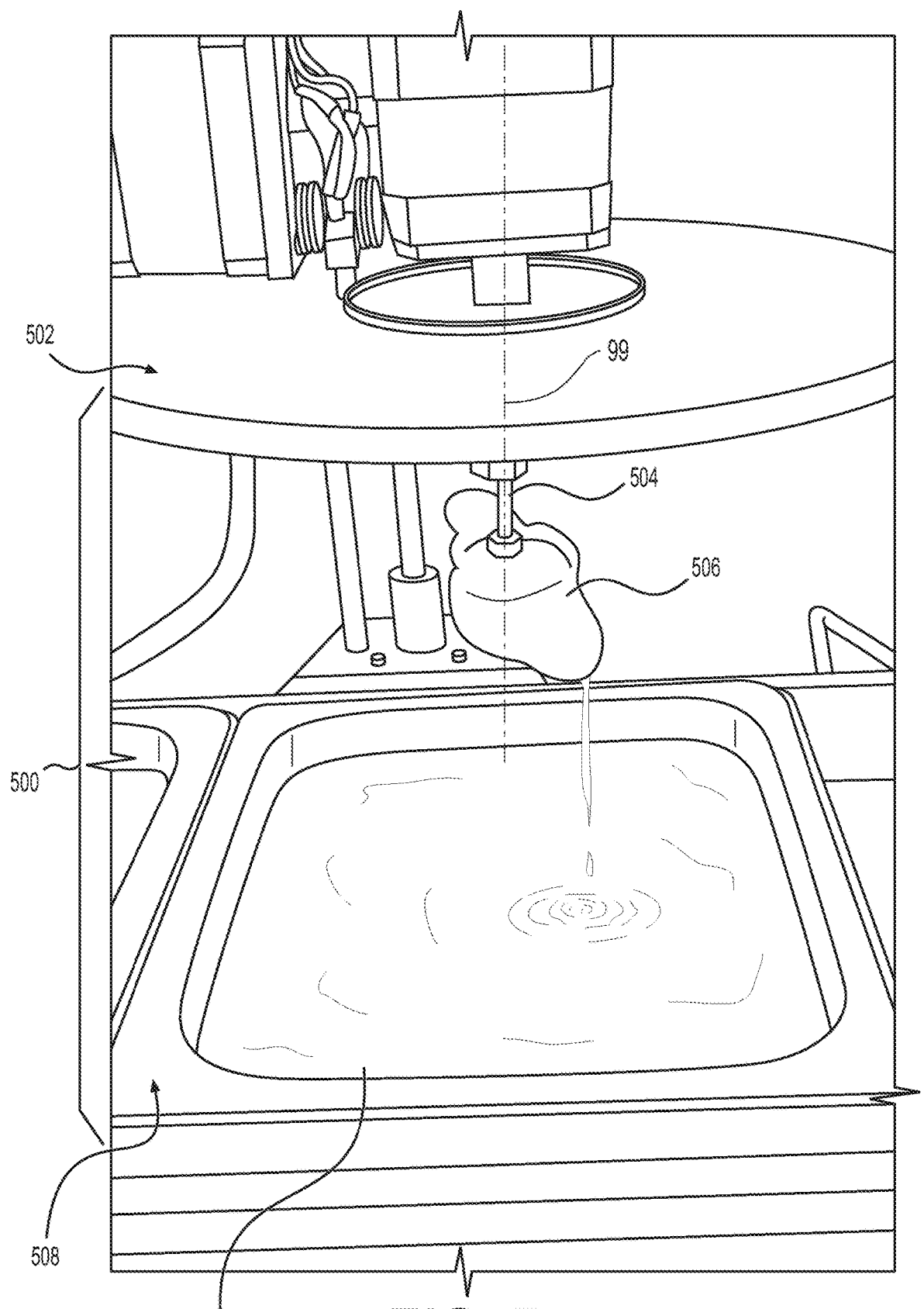
FIG. 5 illustrates a portion of the system of FIG. 2, according to an embodiment of the instant disclosure.

In an embodiment where the system 200 includes at least two of the manufacturing unit 202, the substrate containment unit 204, or the developing unit 206, it is understood that the at least two units may be combined or accommodated jointly to work more succinctly together, for example on a rail system 212, with a gantry feature 214 to move the support structure 100 from one unit to the next during the process of forming the 3D object. Moreover, any one or more of the manufacturing unit 202, the substrate containment unit 204, or the developing unit 206 may include a tool element 216, such as the schematically depicted effector end on the manufacturing unit 202, or as depicted in FIG. 5.

Turning back to the details of the support structure 100, the support structure 100 may be provided as the foundational (i.e., underlying) structural frame of a 3D object. The support structure 100 may be formed, in whole or in part, via a 3D-printer for convenience of continuing with the formation of the axial growth 3D object using the 3D printer, or formed in another suitable manner (i.e., molded, extruded, etc.). As indicated above, the support structure 100 as shown is merely a single example shape of a possible foundational support structure. That is, the support structure 100 has a random shape, as depicted, to focus attention not on the actual shape, but on the applicability of the techniques of axial growth formation with respect to any given shape of a support structure and corresponding completed 3D object using the underlying given shape of the support structure.

Thus, in an embodiment, the support structure 100 may include a body layer 102 connected to one or more intermediate fixture elements, such as intermediate fixture element 104.

The body layer 102 may be shaped to define a corresponding structural shape of the desired 3D object to be formed. As such, the body layer 102 of the support structure 100 provides the outer framing for the axial growth portion of the 3D object formation, discussed further herein. In an embodiment, the body layer 102 includes a mesh layer 106 (or, as depicted in FIG. 3A, a support structure 300 (resembling a human nose) includes a body layer 302 having at least two overlapping mesh layers 302a, 302b). In an embodiment, as shown in FIG. 1, the body layer 102 may further include a non-mesh portion 108, where the surface of the non-mesh portion 108 is substantially continuous compared to the multiple voids and discontinuities in the surface of a mesh layer 106 portion of the body layer 102. Notably, in an embodiment with overlapping mesh layers, the mesh layers may be directly connected along interfacing surface directions or the mesh layers may be loosely adjacent but not directly connected. Additionally, overlapping mesh holes may overlap to create open cells or closed cells, as described herein below with respect to FIGS. 4A and 4B.

In the instant disclosure, the term "mesh," as used with respect to the mesh layer 106 for example, refers to a layer of material having a porous surface that is formed by the cooperation and interconnection of a multitude of branches, such as branch 110, formed by the selected material forming the mesh layer 106 of the support structure (i.e., the material of the mesh layer 106 may be different than the material of the intermediate fixture element 104). The branches may be planar or bend across multiple planes, and extend in various intersecting directions to join ends with other adjacent branches at opposing joinder nodes, such as the joinder nodes 112a, 112b at ends of branch 110. Further, a mesh hole is formed by a plurality of branches aligned so that an aperture void of material exists therebetween. FIG. 1 shows variously sized example mesh holes 114. Thus, mesh holes 114, though varying in size, may be otherwise universally defined as open areas through the surface of the material "layer," formed by interconnected branches. Accordingly, mesh layer 106 includes a plurality of integrally, interconnected mesh holes 114, whether in a same plane or interconnected at adjoining branches that may flex or are intentionally shaped as formed to extend transversely to each other to thereby define a shape of the 3D object.

Though FIG. 1 depicts a body layer 102 that is substantially composed of a mesh layer 106 and a comparatively small non-mesh portion 108, it is considered that a support structure may conversely have a substantial non-mesh portion and a comparatively small mesh layer so as to form what may be considered to be a mesh region of the support structure (not shown explicitly).

As indicated above, in an embodiment, the support structure 100 may be formed by a 3D-printer according to standard protocol instructions, or alternatively, according to a customized algorithmic methodology. For example, an embodiment of a custom algorithmic methodology may include the implementation of a mathematical pattern such as a Voronoi diagram. Moreover, additionally and/or alternatively, a manual alteration of the algorithm via programmable coding of the instructions for a computational processing unit of the system and/or the components thereof (or manual alteration of the printed physical structure) used may further enhance the implementation of standard or modified printing protocols. The manual alteration of the algorithm (or physical structure) may be performed in an effort to alter the arrangement, relative orientation, and/or size (among other properties) of the underlying structure.

It is further contemplated, as indicated above, that the support structure 100 may be formed by manufacturing methods other than 3D printing. That is, it is understood that there may be other methods to create the desired one or more mesh layers, which are significant to the creation of the 3D objects disclosed herein.

As for the intermediate fixture element 104, the intermediate fixture element 104 may have a shape that is different than the outer profile shape of the body layer 102 (i.e., the peripheral shape of the intermediate fixture element 104 that is nearly surrounded by the body layer 102 is substantially cylindrical, whereas the body layer 102 is partially frustro-conical).

In varying embodiments, depending on the configuration, shape, material base type, etc., different support structures may include one or more differently shaped or positioned intermediate fixture elements. In an embodiment, an intermediate fixture element may include, or consist entirely of, a physically supportive structural feature built permanently integrally into (meaning within or about) the support structure with respect to the body layer. This may occur, either simultaneously as part of the build design with the body layer, or as initially positioned in a location on which the body layer may be formed. Moreover, the intermediate fixture element(s) may have one or more mesh layers attached and supported therefrom or therebetween. In an alternative embodiment, the intermediate fixture element may be a physically supportive structural feature that is a prefabricated, non-integrally embedded, structural element so as to be removable and reusable. Additionally, and/or alternatively, an intermediate fixture element may include, or consist entirely of, a sacrificial component, which is understood to be a portion or entirety thereof that is to be destroyed after completion of printing/formation of either the body layer of the support structure, or after completion of the final object. The intermediate fixture element 104 may be any of the above-described versions of intermediate fixture elements (e.g., integral, non-integral, reusable, or sacrificial).

Figure 6:
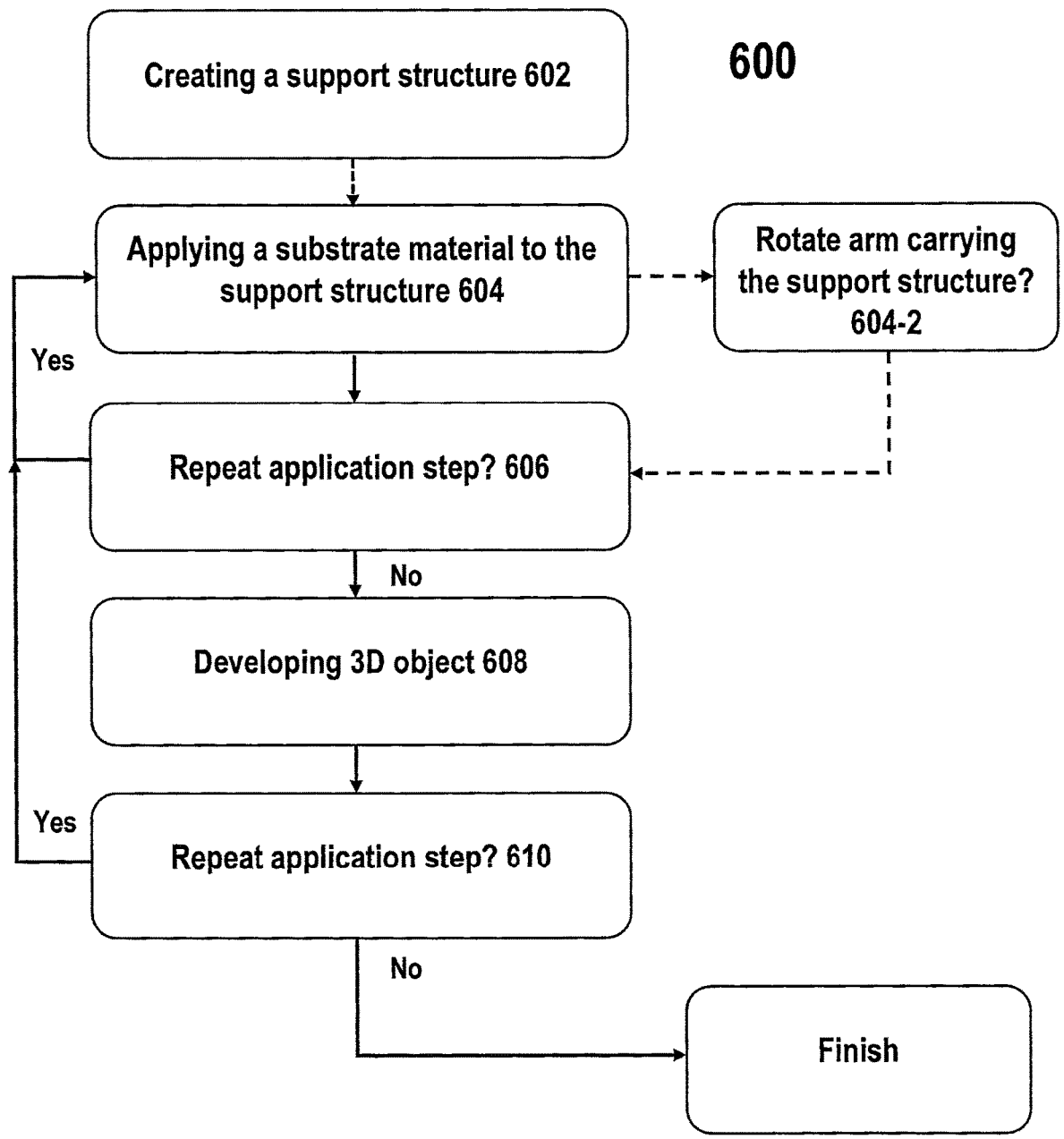
FIG. 6 illustrates a flow diagram of a method of 3D axial growth, according to an embodiment of the instant disclosure.

With respect to the purpose of the intermediate fixture element 104, the 3D object may be formed from the support structure 100 by securing the intermediate fixture element 104 to the one or more tool elements 214 of the system 200, and then completing the implementation of the axial growth process to form the 3D object (as shown in FIG. 6).

As stated above, FIG. 3 depicts a support structure 300, which includes a body layer 302 having at least two overlapping mesh layers 302a, 302b. The curving orientation of the overlapping mesh layers 302a, 302b provide a user with an external profile shape resembling a generic human nose. It is noted here that materials, which may include a collagen substance and/or other biosimilar materials, and which are biocompatible with humans, may be used to form one or both of the support structure 300, and as a substrate material for the additive material layers 304 that form the outer surface of the 3D object (i.e., the fabricated 3D "human" nose 306).

Figure 4A:
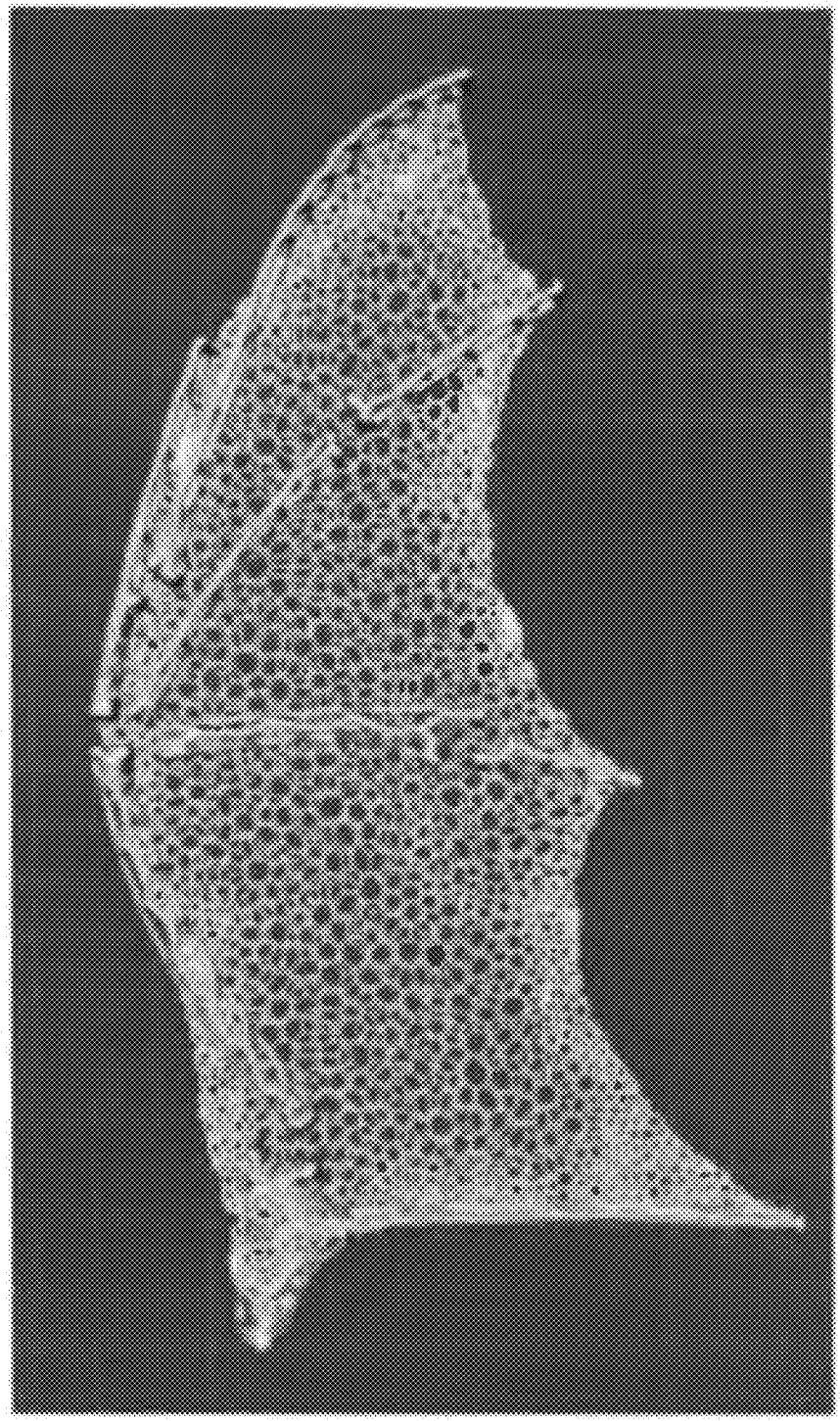
FIG. 4A illustrates a front plane view of a CAD rendered image of an embodiment of an example support structure, according to another embodiment of the instant disclosure.
Figure 4B:
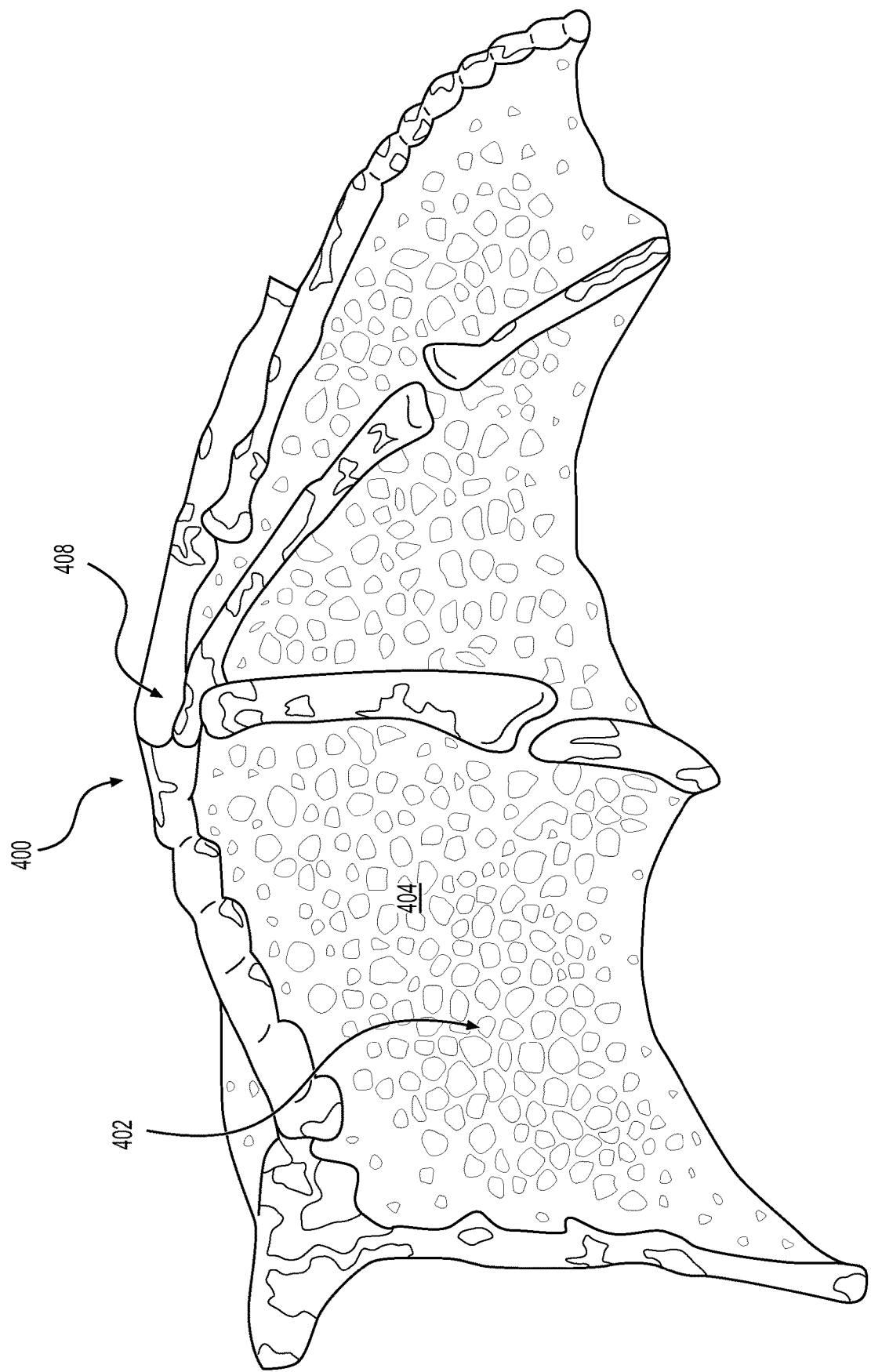
FIG. 4B illustrates a front plane view of a physical model of the support structure depicted as a CAD rendered image in FIG. 4A, after being 3D printed, according to an embodiment of the instant disclosure.
Figure 4C:
FIG. 4C illustrates a front plane view of the 3D object formed via processing the physical model support structure of FIG. 4B, after being further processed by the system of FIG. 2, according to an embodiment of the instant disclosure.

With further respect to overlapping mesh holes, as seen in the model example of a support structure 400 (i.e., resembling a bat's wing) in FIGS. 4A and 4B, the mesh holes may overlap in obstructive or directive paths. In an obstructive path (e.g., a closed cell 402), a mesh hole is sized with respect to the particular consistency, surface tension, and/or viscosity of the substrate material 404, such that upon applying the substrate material 404 (i.e., the additive material layer that is the cured substrate material on the bat's wing shown in FIG. 4C, which in the instant case was a dippable substrate) to the support structure 400, a film layer 406 of the substrate material 404 remains across the mesh hole once removed from the substrate material 404 and obstructs the flow path that would have otherwise existed through the mesh hole. Similarly, where multiple mesh layers are formed, the branches of the adjacent mesh layers may cross directly across the opening of a mesh hole so as to be obstructive to possible flow therethrough, as it is likely to form a film of the additive material across the adjacent mesh holes.

In contrast, in a directive path (e.g., an open cell 408), the mesh holes (or that is to say, the adjoining branches of adjacent mesh holes) do not cross or otherwise significantly block the adjacent mesh hole, and since substrate material will not support a film across the void, a directive path (or a flow pathway) is formed. In a flow pathway, either the mesh hole is sufficiently large, or the collective adjacent mesh holes are sufficiently shaped and aligned such that, upon applying the substrate material 404, a tubular shape forms in an elongated direction so as to prevent a film layer of the additive material from forming across the branches over the voids when curing/drying/reacting to the environment. That is, a film of substrate material may form between the adjacent peripheries of substantially axially aligned mesh holes, but not over the mesh hole between the branches forming the mesh hole itself. As such, where either the mesh holes are open cells, or where the grouping is arranged tubularly (as described immediately above), and assuming the width of the tubular shape is large enough to prevent a film from forming across the end thereof, the collective grouping forms directive paths.

It is contemplated that, upon completion of the 3D object, fluid (e.g., blood, water, saline, etc.) may be passed through the flow pathways, and blocked by closed cells. Thus, the resultant portion of a series of open cells in the 3D object having a flow pathway 410 may be referred to as an integrative intermediate fixture element, a hollow, tunnel structure, like a vein interconnected to other veins via tissue therebetween. Flow pathway 410 is considered an intermediate fixture element because other closed mesh layers, where the cells are blocked by a film after curing the applied substrate material, may be secured thereto and held therebetween.

The mesh pattern and size of the multitude of independent mesh holes formed may vary according to the desired result of the final outcome for the object. This is further determined by the properties (e.g., viscosity, etc.) of the additive material in which the structure is dipped or otherwise applied, as mentioned above. Additionally, the number and density of mesh holes within a particular area may create either a directive path (an open cell) or an obstructive path (a closed cell).

In FIG. 5, an example substrate application unit 500 is depicted. In an embodiment, the substrate application unit 500 may include a rotatable arm 502 rotatable about axis 99 and having a tool element 504 (e.g., end effector) attached thereto. The rotatable arm 502 may be located so as to extend the tool element 504, when holding a support structure 506, axially along axis 99 into a substrate container 508, containing a substrate material 510, such as a dippable bath of fluid substrate, that may form a film across the mesh holes in the mesh layer(s) and/or mesh region(s) of the support structure 506), as depicted.

In an embodiment as depicted in the flow diagram of FIG. 6, a method of 3D axial growth 600 for forming a 3D object may include a step 602 of creating a support structure. The support structure may have a mesh layer or a mesh region. In an embodiment, the step 602 may be achieved using a machine (e.g., a 3D printer, etc.), which may be a first machine.

The method 600 may further include a step 604 of applying a substrate material to the support structure. The application of the substrate material to the support structure may include disposing one or more additive material layers to at least the mesh layer or mesh region to create an axially grown film across the mesh holes. Further, the application of substrate material may include dipping, spraying, blowing, pouring, dusting, etc. the substrate material onto the support structure. Additionally, and/or alternatively, the step 604 may include applying a substrate material to the support structure or a portion thereof, such that subsequent applications of a different substrate material are not effective, thereby preventing additive layering from accumulating upon the support structure or the portion thereof. In an embodiment, the step 604 may use the same machine as in step 602 or may use a second machine different than the first machine. Notably, an intermediary step 604-2 may occur after applying the substrate material, where the rotatable arm carrying the support structure may rotate (e.g., spin axially or in a plane, twirl, etc.) at a predetermined speed to assist in coating the substrate material (e.g., a fluid material) across mesh holes and/or cause the substrate material to exit flow pathways to avoid unnecessary obstruction and minimize post process clearing of material that may have ended up in undesirable locations on the support structure. The rate of rotation, twirling, and/or spinning may vary depending on the additive material properties.

In a step 606 of method 600, the step 604 may be repeated cyclically until the desired 3D object appears according to a predetermined appearance, standard, or other criteria.

In step 606, if it is determined to not repeat step 604, then the process may proceed to the developing stage of step 608 of developing the 3D object. As indicated above, the development unit 206 of the system 200 may involve curing, drying, etc. the added layers of material on the support structure. Moreover, it is contemplated that the intermediate fixture element may be removed, destroyed, or left in place, depending on the situation.

Finally, it is determined in step 610 whether additional application of substrate material should occur by returning to step 604, and if not, then the 3D object is finished.

Additional miscellaneous details that may occur in the method 600 are described herein below.

Once fastened to the tool element of the system, either by remaining attached after a 3D printing process or by removal from another manufacturing process used to form the support structure 100, axial growth may begin to build the 3D object on the body layer 102.

The disclosed axial growth process is particularly well-suited for making components, biological elements, parts, etc. which use a support structure like those described above because of the ability to quickly and easily close the voids across the mesh layer portions of a body layer. This may be achieved at least in part by a dipping process, during which the support structure is dipped into a fluid bath of a desired material, such that the voids of the mesh holes are covered via one or more thin films.

Depending on the material into which the structure is dipped, the support structure with the additive material layer may be subjected during developing to a curing process, which may include exposure to particular wavelengths of light, heat, cold, chemicals, atmosphere, etc., or simply a passage of time. The curing process (if a specific method is needed) may occur after each dipping or after the structure has been dipped multiple times, according to the desired result and the additive material in use to form the outer layer.

Moreover, in an embodiment, with respect to the method step 604, such may more specifically include a step of washing the object in one or more solutions and/or applying inhibitor formulas to avoid substrate contamination. Further, the inhibitor application may aid preventing formation of a closed cell, where an open cell is desired. For example, dipping an object in matching polarity solutions (e.g., alcohol for nonpolar resins, or water for polar substrates (ex.

tissue cultures)) may be used to reduce adhesion of the next layers in small areas. That is, via surface tension/adhesion and capillary action, some solutions may be drawn up into cavities, blocking the adhesion of an additive material and thereby aiding in the development of open tubes.

In an embodiment, the 3D objects created may include biological objects including cartilaginous materials and other tissue types for recreation of biological organs, tissues, etc. In some instances, stem cells and other biological building materials may be implemented as dipping/additive materials to encourage cell and organ growth. It is contemplated that these objects may be used to replace or repair damaged or missing parts in human and animal subjects as the technological capabilities advance. In such instances, the support structure (e.g., scaffolding) may be shaped according to a biological structure's natural shape.

In an embodiment, the objects may further include manual or automated removal of excess additive material left in directive flow paths prior to curing of the additive material. For example, a cotton swab may be passed through an open celled channel.

CONCLUSION

Although several embodiments have been described in language specific to structural features and/or methodological acts, it is to be understood that the claims are not necessarily limited to the specific features or acts described. Rather, the specific features and acts are disclosed as illustrative forms of implementing the claimed subject matter.

What is claimed is:

1. A device for creating a 3D object, with the 3D object formed having a support structure and substrate material, comprising, in combination:
   a manufacturing unit adapted to manufacture the support structure, wherein the support structure comprises a body layer having a mesh layer provided with mesh holes, and a non-mesh portion;
   a substrate application unit adapted to apply substrate material to the support structure, comprising at least one container containing substrate material, and sized to receive the support structure;
   a developing unit for at least one of curing and drying the applied substrate material to form the 3D object;
   a rotatable arm;
   a tool element attached to the rotatable arm, wherein the tool element is extendable axially along an axis into the at least one container and the rotatable arm is rotatable about the axis; and
   an intermediate fixture element adapted to connect the support structure to the tool element such that the support structure is extendable axially along the axis into the at least one container such that the support structure is dipped into the substrate material to coat the support structure with the substrate material.

2. The device for creating the 3D object of claim 1 wherein the 3D object is spun axially along the axis and tilted at the developing unit.

3. The device for creating the 3D object of claim 1 wherein the mesh holes have varying sizes.

4. The device for creating the 3D object of claim 1 wherein the substrate application unit applies an inhibitor at an area of the support structure to inhibit application of the substrate material at the area.

5. The device for creating the 3D object of claim 1 wherein the intermediate fixture element is attached to the support structure at the non-mesh portion, and the intermediate fixture element is formed of a material different than the support structure.

6. A device for creating a 3D object, with the 3D object formed having a support structure and substrate material, comprising, in combination:
   a manufacturing unit adapted to manufacture the support structure, wherein the support structure comprises a body layer having a mesh layer provided with mesh holes, and a non-mesh portion;
   a substrate application unit adapted to apply substrate material to the support structure, comprising at least one container containing substrate material, and sized to receive the support structure;
   a developing unit for at least one of curing and drying the applied substrate material to form the 3D object;
   a rotatable arm;
   a tool element attached to the rotatable arm, wherein the tool element is extendable axially into the at least one container; and
   an intermediate fixture element adapted to connect the support structure to the tool element such that the support structure is extendable axially into the at least one container such that the support structure is dipped into the substrate material to coat the support structure with the substrate material.

* * * * *